United States Patent [19]

Walter

[11] 4,122,702
[45] Oct. 31, 1978

[54] APPARATUS FOR TESTING A FORMS SET FOR PRINT THROUGH QUALITY

[75] Inventor: Alfred Walter, Rietbachstrasse 7, 8952 Schlieren, Switzerland

[73] Assignee: Alfred Walter AG, Schlieren, Switzerland

[21] Appl. No.: 849,015

[22] Filed: Nov. 7, 1977

[30] Foreign Application Priority Data

Feb. 15, 1977 [CH] Switzerland .................. 1869/77

[51] Int. Cl.² ............................................. G01N 3/30
[52] U.S. Cl. ......................................................... 73/14
[58] Field of Search ................................ 73/14, 12, 82

[56] References Cited

U.S. PATENT DOCUMENTS 1,537,179  5/1925  Moller ...................................... 73/14
3,266,289  8/1966  Stamy ....................................... 73/12

Primary Examiner—Jerry W. Myracle
Attorney, Agent, or Firm—Fitch, Even, Tabin & Luedeka

[57] ABSTRACT

Apparatus for testing the print through quality of a forms set. The apparatus comprises a horizontal base plate which is adapted to have the forms set laid thereupon. Sleeve means is mounted above the base plate for guiding a hammer for vertical movement to and from a position where its face strikes the forms set disposed on the base plate. Means are provided for releasably locking the hammer at a preselected one of a plurality of heights above the forms set. A raised test sign is provided on either the face of the hammer or on the upper surface of the base plate below the face of the hammer.

11 Claims, 5 Drawing Figures

APPARATUS FOR TESTING A FORMS SET FOR PRINT THROUGH QUALITY

The present invention relates to testing apparatus and more particularly to apparatus for testing a forms set for print through quality.

Typewriters and mechanical strike, high speed printers used in electronic data processing systems require unit sets or continuous forms sets having a high quality of print through (that is, the dot matrix or standard type printed on the copies in the forms set have sharp edges and good ink covering). The print through quality may be controlled by varying the strengths of strike of the type mechanisms in the typewriter or printer or by the use of different copying materials. Previously, the copying material and the strength of strike has been selected mostly in an empiric way. This was imprecise and led to undesirable differences in quality and costly rejections.

An object of the present invention is the provision of an apparatus for testing print through quality of a forms set.

Other objects and advantages of the present invention will become apparent by reference to the following description and accompanying drawings wherein.

Figure 1:
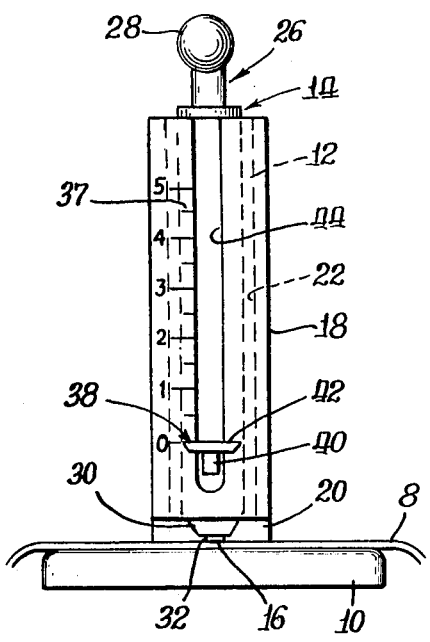
FIG. 1 is a front view of an apparatus for testing the print through quality of a forms set, the forms set being shown in position in the apparatus.

Generally, in accordance with the present invention an apparatus is provided for testing the print through quality of a forms set 8. As disclosed in the drawings, the apparatus comprises a horizontal base plate 10 which is adapted to have the forms set 8 laid thereupon. Sleeve means 12 is mounted above the base plate for guiding a hammer 14 for vertical movement to and from a position where its face strikes the forms set 8 disposed on the base plate 10. Means 15 are provided for releasably locking the hammer 14 at a preselected one of a plurality of heights above the forms set 8. A raised test sign 16 is provided on either the face of the hammer 14 or on the upper surface of the base plate 10 below the face of the hammer 14. Thus, to test the quality of print through, the hammer 14 is raised to a preselected height, the forms set to be tested is placed beneath the face of the hammer, and then the hammer is released. The quality of print through may be determined visually or by instruments.

Figure 2:
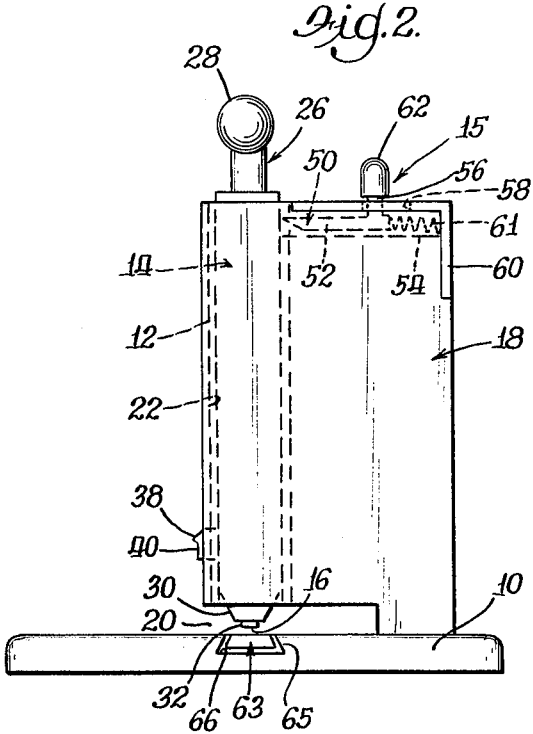
FIG. 2 is a side view of the apparatus shown in FIG. 1, with the forms set removed.
Figure 3:
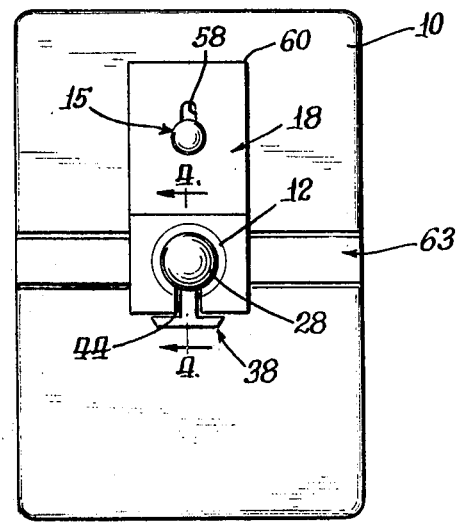
FIG. 3 is a top view of the apparatus shown in FIG. 1, with the forms set removed.

More particularly, as shown in FIGS. 1 to 3, the testing apparatus includes the base plate 10 which is in the form of a generally rectangular plate of structural material, such as aluminum. Attached to the upper surface of the base plate 10, by suitable means, is a standard 18 which contains the sleeve means 12. The illustrated standard 18 is a rectangular block of structural material, such as aluminum, mounted on end adjacent one of the small sides of the base plate 10 and so that its sides are parallel to the long sides of the base plate. The lower surface of the block 18 is recessed so as to provide, together with the upper surface of the base plate 10, a slot 20 for receiving the forms set.

Figure 4:
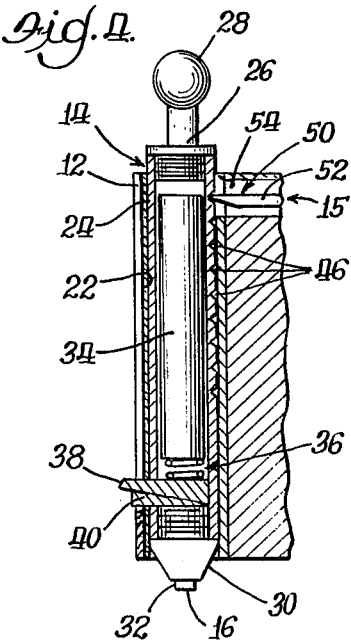
FIG. 4 is a cross-sectional view taken approximately along lines 4—4 of FIG. 3.

The illustrated sleeve means 12, which serves as a guide for the hammer 14, is a tube of bearing material such as bronze disposed in a vertically extending, cylindrical hole or bore 22 disposed in the block 18 above the notch 20. As shown particularly in FIG. 4, the hammer 14 includes a metallic tube 24 of stainless steel having a threaded upper and lower end. The upper end of the tube 24 is closed by a plug 26 of stainless steel having a knob 28 at its upper end. The lower end of the tube 24 is closed by a plug 30, preferably of stainless steel, which is tapered downwardly and is provided at its lower end with a cylindrical striker 32 having a raised test sign. To increase the weight of the hammer, a cylindrical weight 34 is disposed within the tube 24. The weight rests on resilient material 36, a spring or piece of rubber, which prevents the hammer from bouncing back when it strikes the base plate.

The height to which the hammer is lifted is indicated by a scale 37 engraved on the front face of the block 18 and by a pointer 38 attached to the lower portion of the hammer 14. More particularly, the illustrated pointer 38, which is tee shaped, has its stem 40 extending through an opening in the tube 24 and its cross member 42 extending across the front face of the block 18. A vertical slot 44 is provided in the front face of the housing 18 to permit vertical movement of the pointer 38.

Provision is made in the apparatus for releasably locking the hammer 14 at various preselected heights corresponding to the scale 37. In this connection, the rearward surface of the tube 24 is notched to provide a series of vertically spaced teeth 46. The release means 15 is mounted at the upper end of the rear portion of the block 18, which release means 15 includes an "L" shaped bolt 50 having its longer leg 52 riding in a guide slot 54 in the upper face of the block. The front end of the longer leg 52 is pointed so as to engage respective teeth 46. The shorter leg 56 of the bolt 50 extends through a slot 58 in an angle bracket 60, which retains the bolt 50 in the slot, and is provided with a knob 62 at its upper end. The bolt 50 is spring biased toward the hammer 14 by a spring 61.

A removable platen or slide 63 is disposed within the base plate 10 below the hammer 14. As illustrated, the slide 63 is elongated and includes a strip 64 of steel or rubber disposed in a generally U-shaped metal channel 65 of bronze. The slide 60 is disposed in an undercut transversely extending slot 66 in the base plate 10. In the alternate embodiment, wherein the test sign is on the slide 63, the slide 63 is of unitary metallic construction.

Figure 5:
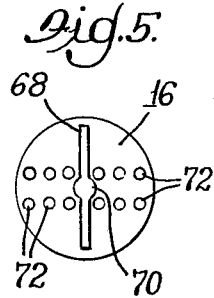
FIG. 5 is an enlarged bottom view of the face of the hammer shown in FIG. 4.

As previously stated, the face or lower end of the striker 32 is provided with a raised test sign 16. Alternately, the slide 63 may be provided with the test sign and the face of striker 32 may be flat. One example of a test sign which permits testing for both dot matrix and character printing is shown in FIG. 5. As shown, the test sign includes an elongated bar 68 with a cylinder 70 at its center. Two rows 72 of three spaced dots each extend perpendicularly to each side of the bar.

In operation, the hammer 14 is raised to a predetermined height where it is automatically locked in position, and the forms set is inserted into the notch 20. The hammer 14 is then released by pulling the bolt 50 whereby the hammer drops and strikes the forms set causing the impression to be made upon the copies. For a quick comparing evaluation, it is sufficient to look at the print through results under a printers glass. A more precise evaluation, which can be recorded, is obtained by measuring the results with suitable test equipment, such as, the conventional Kidder-Tester or the conventional Densitometer. By using the Kidder-Tester the edge sharpness can be evaluated at a magnification of 20 times and the ink covering can be measured by evaluating the difference between the light reflection between the print and unprinted paper surface.

By using the above-described apparatus, it is possible for the first time to obtain precisely reproducible results for comparison which is a big advantage over the prior empirical methods. The selection and evaluation of the copying materials for the forms set may be obtained by prior testing of a sample. Also, the results during production can be controlled as compared to a given standard. Moreover, the incoming materials, namely, self-copying, chemical transfer and one time carbon paper, may be tested for a constant quality of coating and reproduction within the set. In addition, the apparatus permits the testing and calibration of both face and back strike computer printers and/or typewriters.

Various changes and modifications may be made in the above-described apparatus without deviating from the spirit or scope of the present invention. Various features of the invention are set forth in the accompanying claims.

What is claimed is:

1. Apparatus for testing the print through quality of a forms set comprising a base plate adapted to receive the forms set thereon, a hammer, means disposed above said base plate for guiding said hammer for vertical movement to and from a position where the lower face of said hammer strikes the forms set, means for releasably locking said hammer at a plurality of heights above said base plate, the hammer being free falling in said guide means when released by said locking means from each of said heights, and a raised test sign disposed on either the face of said hammer or on the upper surface of the base plate below said face of said hammer, whereby gravity causes said hammer upon being released from a selected one of said heights to drop until the lower face of said hammer strikes the forms set to cause the impression of said test sign to be made on copies included in the forms set.

2. Apparatus according to claim 1 wherein a scale is provided on the guide means, and a pointer is carried by said hammer in position relative to said scale to indicate the height to which the hammer is raised.

3. Apparatus according to claim 1 wherein the hammer is provided with a plurality of notches equally spaced vertically along one side of the hammer and a release device is provided on the guide means and includes a spring held bolt that is adapted to engage the respective notches.

4. Apparatus according to claim 1 wherein the base plate is provided with an exchangeable platen below the face of the hammer.

5. Apparatus for testing the print through quality of a forms set comprising a base plate adapted to receive the forms set thereon, a hammer, means disposed above said base plate for guiding said hammer for vertical movement to and from a position where the lower face of said hammer strikes the forms set, means for releasably locking said hammer at a plurality of heights above said base plate, and a test sign disposed on either the face of said hammer or on the upper surface of the base plate below said face of said hammer, said hammer being hollow, a weight being disposed within said hollow hammer, and a spring means being provided below waid weight in said hammer to prevent said hammer from bouncing back when the hammer strikes the forms set.

6. Apparatus according to claim 5 wherein a scale is provided on the guide means, and a pointer is carried by said hammer in position relative to said scale to indicate the height to which the hammer is raised.

7. Apparatus according to claim 6 wherein the hammer is provided with a plurality of notches equally spaced vertically along one side of the hammer and a release device is provided on the guide means and includes a spring held bolt that is adapted to engage the respective notches.

8. Apparatus according to claim 5 wherein the hammer is provided with a plurality of notches equally spaced vertically along one side of the hammer and a release device is provided on the guide means and includes a spring held bolt that is adapted to engage the respective notches.

9. Apparatus according to claim 5 wherein a scale is provided on the guide means, and a pointer is carried by said hammer in position relative to said scale to indicate the height to which the hammer is raised.

10. Apparatus according to claim 5 wherein the hammer is provided with a plurality of notches equally spaced vertically along one side of the hammer and a release device is provided on the guide means and includes a spring held bolt that is adapted to engage the respective notches.

11. Apparatus according to claim 5 wherein the base plate is provided with an exchangeable platen below the face of the hammer.

* * * * *